United States Patent
Hara et al.

(10) Patent No.: US 11,224,578 B2
(45) Date of Patent: Jan. 18, 2022

(54) MEDICINAL AGENT-CONTAINING MOLECULAR ASSEMBLY WHICH USES AMPHIPHILIC BLOCK POLYMER

(71) Applicants: SHIMADZU CORPORATION, Kyoto (JP); KYOTO UNIVERSITY, Kyoto (JP)

(72) Inventors: Isao Hara, Kyoto (JP); Eiichi Ozeki, Kyoto (JP); Shunsaku Kimura, Kyoto (JP); Takayuki Sato, Osaka (JP)

(73) Assignees: SHIMADZU CORPORATION, Kyoto (JP); KYOTO UNIVERSITY, Kyoto (JP)

( * ) Notice: Subject to any disclaimer, the term of this patent is extended or adjusted under 35 U.S.C. 154(b) by 31 days.

(21) Appl. No.: 16/334,175

(22) PCT Filed: Sep. 20, 2016

(86) PCT No.: PCT/JP2016/077744
§ 371 (c)(1),
(2) Date: May 14, 2019

(87) PCT Pub. No.: WO2018/055681
PCT Pub. Date: Mar. 29, 2018

(65) Prior Publication Data
US 2019/0269624 A1    Sep. 5, 2019

(51) Int. Cl.
*A61K 9/51*    (2006.01)
*A61K 47/14*    (2017.01)
(Continued)

(52) U.S. Cl.
CPC .......... *A61K 9/5123* (2013.01); *A61K 9/1075* (2013.01); *A61K 9/51* (2013.01);
(Continued)

(58) Field of Classification Search
None
See application file for complete search history.

(56) References Cited

U.S. PATENT DOCUMENTS

| 2008/0019908 A1 | 1/2008 | Akitsu et al. |
| 2011/0104056 A1 | 5/2011 | Hara et al. |
(Continued)

FOREIGN PATENT DOCUMENTS

| JP | 4169531 A | 6/1992 |
| JP | 4169532 A | 6/1992 |
(Continued)

OTHER PUBLICATIONS

Cannon, J.B., Strategies to Formulate Lipid-based Drug Delivery Systems, May/Jun. 2011 issue of American Pharmaceutical Review—vol. 14, Issue 4, available at https://www.americanpharmaceuticalreview.com/Featured-Articles/36882-Strategies-to-Formulate-Lipid-based-Drug-Delivery-Systems/.*

(Continued)

*Primary Examiner* — H. Sarah Park
(74) *Attorney, Agent, or Firm* — Sughrue Mion, PLLC (57) ABSTRACT

Provided is a molecular assembly (for example, a polymeric micelle nanoparticle) which is capable of efficiently encapsulating a fat-soluble drug. A molecular assembly comprising: an amphiphilic block polymer A1 comprising a hydrophilic block having a sarcosine unit and a hydrophobic block having a lactic acid unit; a hydrophobic polymer A2 having a lactic acid unit; a fatty acid triglyceride; and a fat-soluble drug. Examples of the fat-soluble drug include miriplatin.

5 Claims, 4 Drawing Sheets

(51) Int. Cl.
| | |
|---|---|
| *A61K 47/34* | (2017.01) |
| *A61K 9/107* | (2006.01) |
| *A61K 33/243* | (2019.01) |
| *B82Y 5/00* | (2011.01) |
| *C08L 77/00* | (2006.01) |

(52) U.S. Cl.
CPC .............. *A61K 47/14* (2013.01); *A61K 47/34* (2013.01); *C08L 77/00* (2013.01); *A61K 9/5153* (2013.01); *A61K 33/243* (2019.01); *B82Y 5/00* (2013.01)

(56) References Cited

U.S. PATENT DOCUMENTS

| | | | |
|---|---|---|---|
| 2013/0149252 A1 | 6/2013 | Hara et al. | |
| 2013/0336896 A1 | 12/2013 | Saji et al. | |
| 2014/0127132 A1 | 5/2014 | Ozeki et al. | |
| 2016/0120985 A1* | 5/2016 | Matsutani | A61K 49/0002 514/772.3 |
| 2017/0151335 A1 | 6/2017 | Suzuki et al. | |

FOREIGN PATENT DOCUMENTS

| | | |
|---|---|---|
| JP | 200824816 A | 2/2008 |
| WO | 2009148121 A1 | 12/2009 |
| WO | 2012026316 A1 | 3/2012 |
| WO | 2012118136 A1 | 9/2012 |
| WO | 2012176885 A1 | 12/2012 |
| WO | WO-2014200007 A1 * 12/2014 | .............. C08L 67/04 |
| WO | 2015178454 A1 | 11/2015 |

OTHER PUBLICATIONS

Communication dated Mar. 30, 2020, from the European Patent Office in application No. 16916752.5.
Akira Makino et al., "Preparation of Novel Polymer Assemblies, "Lactosome", Composed of Poly(L-lactic acid) and Poly(sarcosine)", The Chemistry Society of Japan , vol. 36, No. 10, 2007, pp. 1220-1221, (3 pages total).
Akira Makino et al.,"Near-infrared fluorescence tumor imaging using nanocarrier composed of poly(L-lactic acid)-block-poly(sarcosine) amphiphilic polydepsipeptide", Biomaterials, vol. 30, 2009, pp. 5156-5160 (5 pages total).
International Preliminary Report on Patentability with Translation of Written Opinion dated Apr. 4, 2019, in counterpart International Application No. PCT/JP2016/077744.
International Search Report dated Nov. 22, 2016, in counterpart International Application No. PCT/JP2016/077744.
Chikao Yasuda et al., "In vivo evaluation of microspheres containing the angiogenesis inhibitor, TNP 470, and the metastasis suppression with liver metastatic model implanted neuroblastoma", Pathophysiology, vol. 17, 2010, pp. 149-155 ( 7 pages total).
Communication dated May 9, 2018, from the Taiwanese Intellectual Property Office in application No. 106124120 1.

* cited by examiner

MEDICINAL AGENT-CONTAINING MOLECULAR ASSEMBLY WHICH USES AMPHIPHILIC BLOCK POLYMER

CROSS REFERENCE TO RELATED APPLICATIONS

This application is a National Stage of International Application No. PCT/JP2016/077744 filed Sep. 20, 2016.

TECHNICAL FIELD

The present invention belongs to the fields of nanomedicine and drug delivery system (DDS). The present invention relates to a drug-encapsulating molecular assembly using an amphiphilic block polymer. The drug-encapsulating molecular assembly according to the present invention has a nano-level particle diameter, and can be used as a nano-carrier for delivering various drug substances.

BACKGROUND ART

There has been a growing interest in nanotechnology in recent years. Nanotechnology has been attracting attention in detection of substances in biological samples and in-vivo imaging. Particularly, in the field of medicine and pharmacy, for example, liposome that is a nanoparticle composed of phospholipid is used as a carrier in a drug delivery system (DDS).

JP 1992-169531 A and JP 1992-169532 A, for example, disclose a liposome formulation containing a fat-soluble platinum complex having a saturated or unsaturated higher fatty acid residue as an active ingredient.

On the other hand, peptidic nanoparticles having higher biocompatibility are also known. For example, JP 2008-024816 A and US 2008/0019908 A disclose peptidic nanoparticles using an amphiphilic block polymer having polyglutamic acid methyl ester as a hydrophobic block. The publication indicates that accumulation of the nanoparticles in cancer tissue has been observed.

Further, Chemistry Letters, vol. 36, no. 10, 2007, p. 1220-1221 describes that an amphiphilic block polymer composed of a polylactic acid chain and a polysarcosine chain was synthesized, and a molecular assembly with a particle diameter of 20 to 200 nm having applicability to a nano-carrier in DDS was prepared by self-assembly of the amphiphilic block polymer.

WO 2009/148121 A (US 2011/0104056 A) and Biomaterials, 2009, vol. 30, p. 5156-5160 disclose that a linear amphiphilic block polymer having a polylactic acid chain as a hydrophobic block and a polysarcosine chain as a hydrophilic block self-assembles in an aqueous solution to form a polymeric micelle (lactosome). The particle diameter of the lactosome disclosed in paragraph [0127] in WO 2009/148121 A is 10 nm to 500 nm, but the particle diameter of the lactosome actually demonstrated is only 30 nm to 130 nm disclosed in paragraph [0251]. It is known that the lactosome exhibits high retentivity in blood, and the amount of the lactosome accumulated in the liver is significantly reduced as compared to a polymeric micelle that has been already developed. This lactosome utilizes the property that a nanoparticle with a particle diameter of several tens of nanometers to several hundreds of nanometers retained in blood is likely to be accumulated in cancer (Enhanced Permeation and Retention (EPR) effect), and therefore can be applied as a nano-carrier for cancer site-targeting molecular imaging or drug delivery.

Cells grow faster in cancer tissue than in normal tissue, and therefore formation of new blood vessels is induced in cancer tissue in order to obtain oxygen and energy required for cell growth. It is known that the new blood vessels are brittle, and therefore relatively large molecules also leak from the blood vessels. Further, the substance excretory system of cancer tissue is undeveloped, and therefore molecules leaking from the blood vessels are accumulated in cancer tissue for a certain period of time. This phenomenon is known as EPR effect.

WO 2012/176885 A (US 2014/0127132 A) discloses that a branched amphiphilic block polymer having a branched hydrophilic block containing sarcosine and a hydrophobic block having polylactic acid self-assembles in an aqueous solution to form a polymeric micelle (lactosome) having a particle diameter of 10 to 50 nm.

WO 2012/026316 A (US 2013/0149252 A) and WO 2012/118136 A (US 2013/0336896 A) disclose a switching fluorescent nanoparticle probe composed of a lactosome nanoparticle encapsulating a fluorescent dye, and a fluorescent molecular imaging method using the same.

PRIOR ART DOCUMENTS

Patent Documents

Patent Document 1: JP 1992-169531 A
Patent Document 2: JP 1992-169532 A
Patent Document 3: JP 2008-024816 A
Patent Document 4: US 2008/0019908 A
Patent Document 5: WO 2009/148121 A
Patent Document 6: US 2011/0104056 A
Patent Document 7: WO 2012/176885 A
Patent Document 8: US 2014/0127132 A
Patent Document 9: WO 2012/026316 A
Patent Document 10: US 2013/0149252 A
Patent Document 11: WO 2012/118136 A
Patent Document 12: US 2013/0336896 A Non-Patent Documents Non-Patent Document 1: Chemistry Letters, 2007, Vol. 36, No. 10, p. 1220-1221
Non-Patent Document 2: Biomaterials, 2009, Vol. 30, p. 5156-5160

SUMMARY OF THE INVENTION

Problems to be Solved by the Invention

Since the hydrophobic core of the polymeric micelle (lactosome) nanoparticle disclosed in each of the above publications is composed of polylactic acid, it is difficult to efficiently encapsulate a fat-soluble drug in the hydrophobic core.

It is an object of the present invention to provide a molecular assembly (for example, a polymeric micelle nanoparticle) which is capable of efficiently encapsulating a fat-soluble drug.

Means for Solving the Problems

The present inventors have intensively studied, and as a result, have found that a molecular assembly efficiently encapsulating a fat-soluble drug is obtained by using an amphiphilic block polymer based on polysarcosine/polylactic acid, a hydrophobic polymer based on polylactic acid, and a fatty acid triglyceride, and accomplished the present invention.

The present invention includes the following.

(1) A molecular assembly comprising:

an amphiphilic block polymer A1 comprising a hydrophilic block having a sarcosine unit and a hydrophobic block having a lactic acid unit;

a hydrophobic polymer A2 having a lactic acid unit;

a fatty acid triglyceride; and a fat-soluble drug.

(2) The molecular assembly according to the above item (1), wherein the hydrophilic block contains 2 to 300 sarcosine units.

(3) The molecular assembly according to the above item (1) or (2), wherein the hydrophobic block contains 5 to 400 lactic acid units.

(4) The molecular assembly according to any one of the above items (1) to (3), wherein the hydrophobic polymer A2 contains 10 or more lactic acid units.

(5) The molecular assembly according to any one of the above items (1) to (4), wherein the fatty acid triglyceride is a triester of glycerine and a saturated fatty acid having 4 or more and 24 or less carbon atoms.

(6) The molecular assembly according to any one of the above items (1) to (5), wherein the fat-soluble drug has a saturated or unsaturated aliphatic chain having 4 or more and 24 or less carbon atoms in each molecule.

(7) The molecular assembly according to any one of the above items (1) to (6), wherein a molar ratio A2/A1 of the hydrophobic polymer A2 to the amphiphilic block polymer A1 is in a range of 0.1/1 to 10/1.

(8) The molecular assembly according to any one of the above items (1) to (7), wherein the fatty acid triglyceride is contained in an amount of 5 to 200% by weight with respect to an amount of the amphiphilic block polymer A1.

(9) The molecular assembly according to any one of the above items (1) to (8), wherein the fat-soluble drug is contained in an amount of 1 to 50% by weight with respect to an amount of the amphiphilic block polymer A1.

(10) The molecular assembly according to any one of the above items (1) to (9), which has a particle diameter of 10 to 1,000 nm.

(11) The molecular assembly according to any one of the above items (1) to (10), which is obtained by a preparation method comprising the steps of:

preparing a solution, in a container, containing the amphiphilic block polymer A1, the hydrophobic polymer A2, the fatty acid triglyceride and the fat-soluble drug in an organic solvent;

removing the organic solvent from the solution to obtain a film comprising the amphiphilic block polymer A1, the hydrophobic polymer A2, the fatty acid triglyceride and the fat-soluble drug on an inner wall of the container; and adding water or an aqueous solution into the container to convert the film into a particulate molecular assembly, thereby obtaining a dispersion liquid of the molecular assembly.

A micelle formulation comprising:

an amphiphilic block polymer A1 comprising a hydrophilic block having a sarcosine unit and a hydrophobic block having a lactic acid unit;

a hydrophobic polymer A2 having a lactic acid unit;

a fatty acid triglyceride; and a fat-soluble drug as an active ingredient.

Effects of the Invention

The molecular assembly of the present invention includes an amphiphilic block polymer based on polysarcosine/polylactic acid, a hydrophobic polymer based on polylactic acid, a fatty acid triglyceride, and a fat-soluble drug. By using a fatty acid triglyceride, it is possible to efficiently encapsulate a fat-soluble drug in a hydrophobic core composed of polylactic acid of a polymeric micelle (lactosome) nanoparticle. According to the present invention, there is provided a micelle formulation containing a fat-soluble drug as an active ingredient. Conventionally, a fat-soluble drug is capable of accumulate in the liver due to its nature of auto-agglutinating in the blood; however, the fat-soluble drug is difficult to be delivered to other tumor disease sites. Since the present invention enabled efficient encapsulation of a fat-soluble drug in a lactosome nanoparticle, and stable dispersion of the fat-soluble drug in the blood, drug delivery targeting a tumor disease site is enabled by utilizing the nature of the lactosome nanoparticle of easily accumulating in the tumor disease site [Enhanced Permeability and Retention effect (EPR effect)].

BRIEF DESCRIPTION OF THE DRAWINGS

FIGS. 2 to 5 show time-varying HPLC&ICP-MS measurement charts at 37° C. for a solution of miriplatin-encapsulated lactosome in PBS in the presence of albumin in Experimental example 5.

MODES FOR CARRYING OUT THE INVENTION

A molecular assembly (lactosome) of the present invention is a nanoparticle including: an amphiphilic block polymer A1 comprising a hydrophilic block having a sarcosine unit and a hydrophobic block having a lactic acid unit; a hydrophobic polymer A2 having a lactic acid unit; a fatty acid triglyceride; and a fat-soluble drug. A molecular assembly is formed by agglomeration of amphiphilic block polymer molecules, or by self-assembling oriented association, and the fat-soluble drug is encapsulated in the molecular assembly. The nanoparticle is a nano-order size particle and includes a molecular assembly such as a micelle or a vesicle. Description will be made below.

[1. Amphiphilic Block Polymer A1]

The amphiphilic block polymer A1 comprises a hydrophilic block having a sarcosine unit, and a hydrophobic block having a lactic acid unit. The amphiphilic block polymer may be either linear or branched. The hydrophilic block and the hydrophobic block are linked together by a linker part.

[1-1. Hydrophilic Block]

In the present invention, the specific degree of the physical property, "hydrophilicity" of the hydrophilic block chain is not particularly limited, but, at least, the whole hydrophilic block chain shall be relatively more hydrophilic than the hydrophobic block chain having a lactic acid unit that will be described later. Alternatively, the hydrophilic block chain shall be hydrophilic to such an extent that a copolymer composed of the hydrophilic block chain and the hydrophobic block chain can have amphiphilicity as a whole molecule of the copolymer. Alternatively, the hydrophilic block chain shall be hydrophilic to such an extent that the amphiphilic block polymer can self-assemble in a solvent to form a self-assembly, especially a particulate self-assembly.

In the present invention, the hydrophilic block of the amphiphilic block polymer may have a linear structure or a branched structure. When the hydrophilic block has a branched structure, each of the branches of the hydrophilic block contains sarcosine.

The kind and ratio of a structural unit constituting the hydrophilic block are appropriately determined by those skilled in the art so that a resultant block can have such hydrophilicity as described above as a whole. For example, the hydrophilic block contains 2 to 300 sarcosine units in total. Specifically, when the hydrophilic block has a linear structure, the total number of sarcosine units may be, for example, about 10 to 300, 20 to 200, or 20 to 100. If the number of structural units exceeds the above range, when a molecular assembly is formed, the resultant molecular assembly tends to lack stability. If the number of structural units is less than the above range, a resultant block polymer cannot serve as an amphiphilic block polymer or formation of a molecular assembly tends to be difficult per se.

When the hydrophilic block has a branched structure, the total number of sarcosine units contained in all the branches constituting the hydrophilic block may be, for example, 2 to 200, 2 to 100, or 2 to 10. Alternatively, the total number of sarcosine units contained in all the branches constituting the hydrophilic block may be, for example, 30 to 200 or 50 to 100. The average number of sarcosine units per one branch may be, for example, 1 to 60, 1 to 30, 1 to 10, or 1 to 6. That is, each of the branches constituting the hydrophilic block can be formed to contain sarcosine or a polysarcosine chain. If the number of structural units exceeds the above range, when a molecular assembly is formed, the resultant molecular assembly tends to lack stability. If the number of structural units is less than the above range, a resultant block polymer cannot serve as an amphiphilic block polymer or formation of a molecular assembly tends to be difficult per se.

When the hydrophilic block has a branched structure, the number of branches of the hydrophilic block shall be 2 or more, but is preferably 3 or more from the viewpoint of efficiently obtaining a particulate micelle when a molecular assembly is formed. The upper limit of the number of branches of the hydrophilic block is not particularly limited, but is, for example, 27. Particularly, in the present invention, the number of branches of the hydrophilic block is preferably 3. The branched structure can be appropriately designed by those skilled in the art.

Sarcosine (i.e., N-methylglycine) is highly water-soluble, and a sarcosine polymer is highly flexible, because the polymer has an N-substituted amide and therefore can be more easily cis-trans isomerized as compared to a normal amide group, and steric hindrance around the $C^\alpha$ carbon atom is low. The use of such a structure as a constituent block is very useful in that the block can have high hydrophilicity as its basic characteristic, or both high hydrophilicity and high flexibility as its basic characteristics.

Further, the hydrophilic block preferably has a hydrophilic group (typified by, for example, a hydroxyl group) at its end (i.e., at the end opposite to a linker part).

In the polysarcosine chain, all the sarcosine units may be either continuous or discontinuous. However, it is preferred that the branched chain is molecularly-designed so that the basic characteristics thereof described above are not impaired as a whole.

When the hydrophilic block chain has another structural unit other than a sarcosine unit, such another structural unit is not particularly limited, but may be amino acid (including hydrophilic amino acids and other amino acid). It is to be noted that the term "amino acid" used in this specification includes natural amino acids, unnatural amino acids, and derivatives thereof obtained by modification and/or chemical alteration. Further, in this specification, the term "amino acid" includes $\alpha$-, $\beta$-, and $\gamma$-amino acids. Among them, $\alpha$-amino acids are preferred. Examples of $\alpha$-amino acids include serine, threonine, lysine, aspartic acid, glutamic acid, and the like.

Further, the amphiphilic block polymer A1 may further have a group such as a sugar chain or polyether. In this case, the amphiphilic block polymer A1 is preferably molecularly-designed so that the hydrophilic block has a sugar chain or polyether.

[1-2. Hydrophobic Block]

In the present invention, the specific degree of the physical property, "hydrophobicity" of the hydrophobic block is not particularly limited, but, at least, the hydrophobic block shall be hydrophobic enough to be a region relatively more hydrophobic than the whole hydrophilic block so that a copolymer composed of the hydrophilic block and the hydrophobic block can have amphiphilicity as a whole molecule of the copolymer, or so that the amphiphilic block polymer can self-assemble in a solvent to form a self-assembly, preferably a particulate self-assembly.

The hydrophobic block present in one amphiphilic block polymer may or may not be branched. However, it is considered that when the hydrophobic block is not branched in consideration of a molecular assembly such as a micelle structure, a stable core/shell-type micelle having a smaller particle diameter can be easily formed, because a hydrophilic branched shell part is denser than a hydrophobic core.

In the present invention, the hydrophobic block contains a lactic acid unit. The kind and ratio of a structural unit constituting the hydrophobic block are appropriately determined by those skilled in the art so that a resultant block can have such hydrophobicity as described above as a whole. For example, the number of lactic acid units contained in the hydrophobic block is 5 to 400. Specifically, for example, when the hydrophobic block is not branched, the number of lactic acid units may be, for example, 5 to 100, 15 to 60, or 25 to 45. When the hydrophobic block is branched, the total number of lactic acid units contained in all the branches constituting the hydrophobic block may be, for example, 10 to 400, preferably 20 to 200. In this case, the average number of lactic acid units per one branch is, for example, 5 to 100, preferably 10 to 100.

If the number of structural units exceeds the above range, when a molecular assembly is formed, the resultant molecular assembly tends to lack stability. If the number of structural units is less than the above range, formation of a molecular assembly tends to be difficult per se.

When the hydrophobic block is branched, the number of branches is not particularly limited, but may be, for example, equal to or less than the number of branches of the hydrophilic block from the viewpoint of efficiently obtaining a particulate micelle when a molecular assembly is formed.

Polylactic acid has the following basic characteristics.

Polylactic acid has excellent biocompatibility and stability. Therefore, a molecular assembly obtained from an amphiphilic material having such polylactic acid as a constituent block is very useful from the viewpoint of applicability to a living body, especially a human body.

Further, polylactic acid is rapidly metabolized due to its excellent biodegradability, and is therefore less likely to accumulate in tissue other than cancer tissue in a living body. Therefore, a molecular assembly obtained from an amphiphilic material having such polylactic acid as a constituent block is very useful from the viewpoint of specific accumulation in cancer tissue.

Further, polylactic acid is excellent in solubility in low-boiling point solvents. This makes it possible to avoid the use of a hazardous high-boiling point solvent when a molecular assembly is obtained from an amphiphilic material having such polylactic acid as a constituent block. Therefore, such a molecular assembly is very useful from the viewpoint of safety for a living body.

It is to be noted that, in a polylactic acid chain (PLA) constituting the hydrophobic block, all the lactic acid units may be either continuous or discontinuous. However, it is preferred that the hydrophobic block is molecularly-designed so that the basic characteristics described above are not impaired as a whole.

The polylactic acid chain (PLA) constituting the hydrophobic block may be either a poly L-lactic acid chain (PLLA) constituted from L-lactic acid units, or a poly D-lactic acid chain (PDLA) constituted from D-lactic acid units. Alternatively, the PLA may be constituted from both L-lactic acid units and D-lactic acid units. In this case, the arrangement of L-lactic acid units and D-lactic acid units may be any one of alternate arrangement, block arrangement, and random arrangement.

When the hydrophobic block chain has another structural unit other than a lactic acid unit, the kind and ratio of such another structural unit are not particularly limited as long as a resultant block chain can have such hydrophobicity as described above as a whole, but the hydrophobic block chain is preferably molecularly-designed to have desired various characteristics.

When the hydrophobic block chain has another structural unit other than a lactic acid unit, such another structural unit can be selected from the group consisting of hydroxy acids other than lactic acid and amino acids (including hydrophobic amino acids and other amino acids). Examples of hydroxy acids include, but are not limited to, glycolic acid, hydroxyisobutyric acid, and the like. Many of hydrophobic amino acids have an aliphatic side chain, an aromatic side chain, and the like. Examples of natural amino acids include glycine, alanine, valine, leucine, isoleucine, proline, methionine, tylosin, tryptophan, and the like. Examples of unnatural amino acids include, but are not limited to, amino acid derivatives such as methyl glutamate, benzyl glutamate, methyl aspartate, ethyl aspartate, and benzyl aspartate.

[1-3. Structure of Amphiphilic Block Polymer A1]

The structure of the linker site that links the hydrophilic block and the hydrophobic block together is not particularly limited as long as it is a chemically acceptable structure, in case that the amphiphilic block polymer A1 is either linear or branched.

WO 2009/148121 A (linear type) and WO 2012/176885 A (branched type) can be referred to for the structure and synthesis of the amphiphilic block polymer A1, and the amphiphilic block polymer A1 can be appropriately molecularly-designed by those skilled in the art.

When the hydrophilic block has a branched structure, for example, when the number of branches of the hydrophilic block side is 2, two molecular chains containing a polysarcosine chain may extend as branches from one N atom present in the linker site of a molecular chain containing a polylactic acid chain. In other words, an N atom directly or indirectly bound to a polylactic acid chain may be directly or indirectly bound to two polysarcosine chains.

Further, for example, when the number of branches of the hydrophilic block side is 3, three molecular chains containing a polysarcosine chain may extend as branches from one C atom present in the linker site of a molecular chain containing a polylactic acid chain. In other words, a C atom directly or indirectly bound to a polylactic acid chain may be directly or indirectly bound to three polysarcosine chains. The same applies when branching occurs at one P or Si atom present in the linker site, or when the whole molecule of the amphiphilic block polymer forms a quaternary ammonium molecule.

When the number of branches of the hydrophilic block side exceeds 3, the hydrophilic block side can be molecularly-designed so that the branches further have a branched structure.

When the hydrophobic block side is also branched, the hydrophobic block side can be molecularly-designed from the same viewpoint as described above.

A preferred structure of the branched-type amphiphilic block polymer in which the number of branches of the hydrophilic block side is 3 and the hydrophobic block side is not branched is represented by the following formula (I).

[Chemical Formula 1]

(I)

In the formula (I), n1, n2 and n3 represent numbers whose sum is 3 to 200, m represents a number of 5 to 100, and R represents a hydrogen atom or an organic group. The number of carbon atoms in the organic group may be 1 to 20.

Specific examples of the organic group include alkyl groups, alkylcarbonyl groups, and the like.

A preferred structure of the branched-type amphiphilic block polymer in which the number of branches of the hydrophilic block side is 3 and the number of branches of the hydrophobic block side is 2 is represented by the following formula (II)

[Chemical Formula 2]

(II)

In the formula (II), n1, n2, and n3 and R are the same as those in the formula (I) and m1 and m2 represent numbers whose sum is 10 to 400.

[1-4. Synthesis of Amphiphilic Block Polymer A1]

In the present invention, a method for synthesizing the amphiphilic block polymer A1 is not particularly limited, and a known peptide synthesis method, a known polyester synthesis method, and/or a known depsipeptide synthesis method can be used.

Peptide synthesis can be performed by, for example, ring-opening polymerization of N-carboxyamino acid anhydride (amino acid NCA) using, as an initiator, a base such as an amine.

Polyester synthesis can be performed by, for example, ring-opening polymerization of lactide using, as an initiator, a base such as an amine or a metal complex. The type of lactide can be appropriately determined by those skilled in the art in consideration of the desired optical purity of a resultant block chain. For example, the type of lactide can be appropriately selected from L-lactide, D-lactide, DL-lactide and mesolactide, and the amount of lactide to be used can be appropriately determined by those skilled in the art depending on the desired optical purity of a resultant block chain.

Depsipeptide synthesis can be performed by, for example, a method in which polylactic acid is first synthesized as a hydrophobic block and then a polypeptide chain is extended as a hydrophilic block; or a method in which a polypeptide chain is first synthesized as a hydrophilic block and then polylactic acid is extended as a hydrophobic block.

In the molecular assembly according to the present invention, the chain length of polylactic acid can be adjusted. From the viewpoint of more flexibly controlling the chain length of polylactic acid, synthesis of the amphiphilic block polymer A1 is preferably performed by a method in which polylactic acid is first synthesized as a hydrophobic block and then a polypeptide chain is extended as a hydrophilic block chain. Further, the polymerization degree of polylactic acid as a hydrophobic block chain in the amphiphilic block polymer A1 can be more easily and accurately controlled than that of polysarcosine as a hydrophilic block chain.

Furthermore, WO 2009/148121 A (linear type) and WO 2012/176885 A (branched type) can be referred to for the synthesis of the amphiphilic block polymer A1.

[2. Hydrophobic Polymer A2]

The hydrophobic polymer A2 is a hydrophobic polymer having lactic acid units. The hydrophobic polymer A2 has, for example, 10 or more lactic acid units, and preferably has 15 or more lactic acid units. Here, the specific degree of "hydrophobicity" of the hydrophobic polymer A2 is not particularly limited, but at least, the hydrophobic polymer A2 is relatively more hydrophobic than the hydrophilic block of the amphiphilic polymer A1.

It is preferred that the hydrophobic polymer A2 is mainly composed of 10 or more lactic acid units. However, the hydrophobic polymer A2 may have another structural unit other than a lactic acid unit. All the lactic acid units may be either continuous or discontinuous.

The kind of structural unit and the chain length of the hydrophobic polymer A2 may be basically determined from the same point of view as in the case of the molecular design of the hydrophobic block chain of the amphiphilic block polymer A1. This makes it possible to obtain the effect that the hydrophobic polymer A2 can have excellent affinity for the hydrophobic block chain of the amphiphilic block polymer A1 in a resultant molecular assembly. It is considered that the hydrophobic polymer A2 exists mainly in a hydrophobic core part of a micelle molecular assembly composed of the amphiphilic block polymer A1.

A polylactic acid chain (PLA) constituting the hydrophobic polymer A2 may be either a poly-L-lactic acid chain (PLLA) composed of L-lactic acid units or a poly-D-lactic acid chain (PDLA) composed of D-lactic acid units. Further, a polylactic acid chain (PLA) constituting the hydrophobic polymer A2 may be constituted from both L-lactic acid units and D-lactic acid units. In this case, the arrangement of L-lactic acid units and D-lactic acid units may be any one of alternate arrangement, block arrangement, and random arrangement. When the polylactic acid chain (PLA) constituting the hydrophobic polymer A2 is constituted from both L-lactic acid units and D-lactic acid units, the polylactic acid chain (PLA) tends to be an amorphous polymer. The amorphous polymer refers to a polymer whose melting point is not measured in accordance with JIS K7121.

In a case where the hydrophobic polymer A2 has another structural unit other than a lactic acid unit, the another structural unit is contained in the hydrophobic polymer A2 to the extent that the hydrophobic polymer A2 does not impinge on deviating from the above-defined "hydrophobicity" as a whole. Therefore, the another structural unit may be either more hydrophilic or more hydrophobic than a lactic acid unit. The kind and the ratio of the another structural units constituting the hydrophobic polymer A2 are appropriately determined by those skilled in the art so that the hydrophobic polymer A2 can have such hydrophobicity as described above as a whole. Examples of the another structural unit include those mentioned in the above item 1-2 as structural units other than a lactic acid unit.

While the upper limit of the number of structural units of the hydrophobic polymer A2 is not particularly limited, for example, it should be selected so as not to exceed the length of twice the hydrophobic block in the amphiphilic block polymer A1. Specifically, in the case of an unbranched hydrophobic block of the polymer A1, for example, when the number of lactic acid units in the hydrophobic block of the polymer A1 is, for example, 5 to 100, 15 to 60, or 25 to 45, the upper limit of the number of structural units of the hydrophobic polymer A2 can be about 10 to 200, 30 to 120, or 50 to 90 in correspondence with the number of lactic acid units. In the case of a branched hydrophobic block of the polymer A1, when an average number of lactic acid units per one branch in the hydrophobic block of the polymer A1 is, for example, 5 to 100, preferably 10 to 100, the upper limit of the number of structural units of the hydrophobic polymer A2 can be about 10 to 200, 20 to 200 in correspondence with the number of lactic acid units. However, when the polylactic acid chain (PLA) constituting the hydrophobic polymer A2 is an amorphous polymer, a longer chain exceeding 5 folds the length of the hydrophobic block in the amphiphilic block polymer A1 may be used. The stability of the formed molecular assembly, and the hydrophobic core volume and the particle diameter of the molecular assembly can be adjusted by the number of structural units of the hydrophobic polymer A2.

The hydrophobic polymer A2 can be synthesized by a polymerization method known to those skilled in the art. For example, the polylactic acid may be synthesized by ring-opening polymerization of lactide with reference to WO 2009/148121 A ([0239] to [0241]). Alternatively, the polylactic acid may be synthesized by direct polymerization of lactic acid.

The hydrophobic polymer A2 is not particularly limited, but is contained in a molar ratio A2/A1 to the amphiphilic block polymer A1 in a range of 0.1/1 to 10/1, for example. The hydrophobic core volume and the particle diameter of the molecular assembly can be adjusted by the mixing amount of the hydrophobic polymer A2. When the ratio of the hydrophobic polymer A2 is more than the aforementioned range, the molecular assembly itself tends to be difficult to keep its shape. When the ratio of the hydrophobic polymer A2 is less than the aforementioned range, the effect of mixing the hydrophobic polymer A2 (that is, the effect of increasing the hydrophobic core volume and the effect of controlling the particle diameter) tends to be difficult to be obtained. A preferred molar ratio A2/A1 is in a range of 0.5/1 to 2.5/1.

By using the amphiphilic block polymer A1 and the hydrophobic polymer A2 in amounts satisfying the above range, it is possible to prepare a molecular assembly having a particle diameter of, for example, 10 to 1000 nm, 10 to 500 nm, preferably 10 to 200 nm, more preferably 20 to 100 nm. The term "particle diameter" used herein refers to a particle diameter occurring most frequently in particle size distribution, that is, a mode particle diameter. A method for measuring the size of the molecular assembly nanoparticle according to the present invention is not particularly limited, and is appropriately selected by those skilled in the art. Examples of such a method include an observation method with a TEM (Transmission Electron Microscope) or an AFM (Atomic Force Microscope), a static light scattering method, and a DLS (Dynamic Light Scattering) method. In the case of a DLS method, the translational diffusion coefficient of particles undergoing Brownian movement in a solution is measured. In the examples of this specification, a dynamic light scattering method is used.

[3. Fatty Acid Triglyceride]

The fatty acid triglyceride is a triester of glycerin and a fatty acid. Fatty acid triglycerides can be classified into short-chain fatty acid triglyceride (SCT) (generally those having 5 or less carbon atoms in the fatty acid), medium-chain fatty acid triglyceride (MCT) (generally those having 6 or more and 12 or less carbon atoms in the fatty acid), and long-chain fatty acid triglyceride (LCT) (generally those having 13 or more carbon atoms in the fatty acid) depending on the number of carbons in the fatty acid.

Examples of the short-chain fatty acid in the short-chain fatty acid triglyceride include saturated fatty acids having 2 to 5 carbon atoms, and more specific examples include acetic acid ($C_2$), propionic acid ($C_3$), butyric acid ($C_4$), isobutyric acid ($C_4$), valeric acid ($C_5$), and isovaleric acid ($C_5$).

Examples of the middle-chain fatty acid in the middle-chain fatty acid triglyceride include saturated fatty acids having 6 to 12 carbon atoms, and more specific examples include caproic acid ($C_6$), enanthic acid ($C_7$), caprylic acid ($C_8$), pelargonic acid ($C_9$), capric acid ($C_{10}$), undecylic acid ($C_{11}$), and lauric acid ($C_{12}$).

Examples of the long-chain fatty acid in the long-chain fatty acid triglyceride include saturated fatty acids having 13 or more carbon atoms, and more specific examples include pentadecylic acid (C15), palmitic acid (C16), margaric acid (C17), stearic acid (C18), arachidic acid (C20), behenic acid (C22), and lignoceric acid (C24).

In the present invention, as the fatty acid triglyceride, a triester of glycerin and a saturated fatty acid having about 4 to 24 carbon atoms may be used, a triester of glycerin and a saturated fatty acid having about 6 to 20 carbon atoms is preferably used, and a triester of glycerin and a saturated fatty acid having about 8 to 20 carbon atoms is more preferably used. Further, a middle-chain fatty acid triglyceride having 8 to 12 carbon atoms is more preferably used.

In the triglyceride molecule, the three esters may be esters with the same middle-chain fatty acid, or may be esters with different middle-chain fatty acids. All of these are liquid oils. As the middle-chain fatty acid triglyceride, a commercial product is available. For example, as (caprylic acid/capric acid) triglyceride, O.D.O [(caprylic acid/capric acid)=75/25], Scholey 64G [(caprylic acid/capric acid)=60/40], Scholey MC [(caprylic acid/capric acid)=85/15], Scholey 8 [caprylic acid=95% or more] (these are available from The Nisshin OilliOGroup, Ltd.); COCONARD ML[(caprylic acid/capric acid/lauric acid)triglyceride], COCONARD MT [(caprylic acid/capric acid)triglyceride], COCONARD RK[(caprylic acid)triglyceride] (these are available from Kao Corporation) and the like are recited.

The fatty acid triglyceride, in particular, the middle-chain fatty acid triglyceride is well miscible with the hydrophobic polymer A2, and is considered as being mainly present in the hydrophobic core part of the molecular assembly micelle composed of the amphiphilic block polymer A1. By mixing the fatty acid triglyceride, in particular, the middle-chain fatty acid triglyceride, it is possible to efficiently encapsulate the fat-soluble drug in the hydrophobic core part of the molecular assembly micelle.

Although not particularly limited, the fatty acid triglyceride is contained, for example, in an amount of 5 to 200% by weight with respect to the amphiphilic block polymer A1. It is possible to adjust the encapsulated amount of the fat-soluble drug by the mixing amount of the fatty acid triglyceride. The effect in encapsulation of the fat-soluble drug is easily obtained by the amount of the middle-chain fatty acid triglyceride of about 5 to 200% by weight. On the other hand, when the amount of the middle-chain fatty acid triglyceride is more than the above range, the volume space of the hydrophobic core part of the molecular assembly micelle decreases, and the encapsulating effect of the fat-soluble drug tends to deteriorate. The amount of the middle-chain fatty acid triglyceride is preferably in a range of 5 to 100% by weight, and more preferably in a range of 10 to 50% by weight with respect to the amphiphilic block polymer A1.

[4. Fat-Soluble Drug]

The fat-soluble drug is a drug having a saturated or unsaturated aliphatic chain having 4 to 24 carbon atoms in each molecule. As the aliphatic chain having 4 to 24 carbon atoms, saturated or unsaturated, lower or higher aliphatic hydrocarbon groups, and saturated or unsaturated, lower or higher fatty acid residues can be recited.

As the saturated or unsaturated, lower aliphatic hydrocarbon groups, hydrocarbon groups having 4 to 7 carbon atoms can be recited, and examples of such hydrocarbon groups include alkyl groups such as a butyl group, a pentyl group, a hexyl group, a 2-ethylhexyl group, and a heptyl group; and alkenyl groups such as a butenyl group, a pentenyl group, a hexenyl group, and a heptenyl group.

As the saturated or unsaturated, higher aliphatic hydrocarbon groups, hydrocarbon groups having 8 to 24 carbon atoms can be recited, and examples of such hydrocarbon groups include alkyl groups such as an octyl group, a nonyl group, a decyl group, a dodecyl group, a tetradecyl group, a hexadecyl group and an octadecyl group; and alkenyl groups such as a decenyl group, a dodecenyl group, a tetradecenyl group, a hexadecenyl group, and an octadecenyl group.

As the saturated or unsaturated higher fatty acid residues, fatty acid residues having 8 to 24 carbon atoms can be recited, and examples of such fatty acid residues include saturated fatty acid residues such as octylic acid ($C_8$), nonylic acid ($C_9$), capric acid ($C_{10}$), undecylic acid ($C_{11}$), lauric acid ($C_{12}$), myristic acid ($C_{14}$), palmitic acid ($C_{16}$), stearic acid ($C_{18}$), arachidic acid ($C_{20}$), behenic acid ($C_{22}$), and lignoceric acid ($C_{24}$); and unsaturated fatty acid residues such as palmitoleic acid ($C_{16}$), oleic acid ($C_{18}$), linolic acid ($C_{18}$), linolenic acid ($C_{18}$), and arachidonic acid ($C_{20}$). The fatty acid residues include the form of a fatty acid (—COOH), the form of a salt of fatty acid (—COO$^-$), the form of a fatty acid constituting a complex with metal, and the form of a fatty acid derivative (esterified).

In the present invention, the fat-soluble drug preferably has a saturated or unsaturated aliphatic chain (the aforementioned aliphatic hydrocarbon group, or fatty acid residue) having about 4 to 20 carbon atoms in each molecule.

The fat-soluble drug may have one aliphatic chain as described above, or may have two or more aliphatic chains in each molecule. The fat-soluble drug may be a complex containing metal such as platinum, zinc, iron, copper or the like.

One exemplary fat-soluble drug is a complex in which two saturated or unsaturated higher fatty acid residues, and two amines (substituted with an organic group or unsubstituted) coordinate with platinum. One specific example is miriplatin [Miripla (registered trade name), (SP-4-2)-[(1R, 2R)-cyclohexane-1,2-diamine-N,N'] bis (tetradecanoato-O) platinum] which is a complex in which two myristic acid ($C_{14}$) residues and diaminocyclohexane coordinate with platinum. Miriplatin is a platinum-based anticancer drug.

Since bulk particles of miriplatin are capable of agglomerate one another ("Research and Development for novel hepatoma therapeutic agent, Miriplatin", Sumitomo Chemical Co., Ltd., 2011-I, pp 39-46), the phenomenon that miriplatin agglomerates and miriplatin is excluded outside the system is observed in the operation of forming a molecular assembly micelle. For this reason, it is difficult to efficiently encapsulate the fat-soluble drug such as miriplatin in the hydrophobic core part of the molecular assembly micelle composed of the amphiphilic block polymer A1. In the present invention, it is possible to efficiently encapsulate the fat-soluble drug in the hydrophobic core part of the molecular assembly micelle by mixing the middle-chain fatty acid triglyceride.

Although not particularly limited, the fat-soluble drug can be efficiently contained, for example, in an amount of 1 to 50% by weight, preferably in an amount of 1 to 30% by weight, occasionally in an amount of 1 to 10% by weight with respect to the amphiphilic block polymer A1.

[5. Formation of Molecular Assembly]

A method for forming the molecular assembly (lactosome) is not particularly limited, and can be appropriately selected by those skilled in the art depending on, for example, the desired size and characteristics of the molecular assembly and the kind, properties, and amount of a functional structure to be carried by the molecular assembly. If necessary, after being formed by a method that will be described later, the resultant molecular assembly may be surface-modified by a known method. It is to be noted that whether particles have been formed or not may be confirmed by observation with an electron microscope.

[5-1. Film Method]

The amphiphilic block polymer A1, the hydrophobic polymer A2, the medium-chain fatty acid triglyceride and the fat-soluble drug used in the present invention are soluble in low-boiling point solvents, and therefore the molecular assembly can be prepared by a film method.

The film method includes the following steps of: preparing a solution, in a container (e.g., a glass container), containing the amphiphilic block polymer A1, the hydrophobic polymer A2, the fatty acid triglyceride and the fat-soluble drug in an organic solvent; removing the organic solvent from the solution to obtain a film comprising the amphiphilic block polymer A1, the hydrophobic polymer A2, the fatty acid triglyceride and the fat-soluble drug on an inner wall of the container; and adding water or an aqueous solution into the container, and if necessary, performing ultrasonic treatment to convert the film into a particulate molecular assembly (having the fat-soluble drug encapsulated therein), thereby obtaining a dispersion liquid of the molecular assembly. Further, the film method may include the step of subjecting the dispersion liquid of the molecular assembly to freeze-drying treatment.

The solution containing the amphiphilic block polymer A1, the hydrophobic polymer A2, the fatty acid triglyceride and the fat-soluble drug in an organic solvent is appropriately prepared by those skilled in the art. For example, the solution may be prepared by mixing, at a time, all the polymers A1 and A2, the fatty acid triglyceride and the fat-soluble drug that should be used; or the solution may be prepared by previously preparing a film of one or two component(s) of the polymers A1 and A2, the fatty acid triglyceride and the fat-soluble drug that should be used (e.g., the polymer A1 component), and then adding a solution containing the other component(s) that should be used (e.g., the polymer A2, the fatty acid triglyceride and the fat-soluble drug). The previously-prepared film of one of the polymers may be formed in accordance with a method that will be described later (i.e., a method for forming a film comprising the polymers A1 and A2, the fatty acid triglyceride and the fat-soluble drug).

The organic solvent used in the film method is preferably a low-boiling point solvent. In the present invention, the term "low-boiling point solvent" refers to one whose boiling point is 100° C. or less, preferably 90° C. or less at 1 atmospheric pressure. Specific examples of such a low-boiling point solvent include chloroform, diethyl ether, acetonitrile, 2-propanol, ethanol, acetone, dichloromethane, tetrahydrofuran, hexane, and the like.

When such a low-boiling point solvent is used for dissolving the polymers A1 and A2, the fatty acid triglyceride and the fat-soluble drug, solvent removal can be very easily performed. A method for solvent removal is not particularly limited, and may be appropriately determined by those skilled in the art depending on, for example, the boiling point of an organic solvent to be used. For example, solvent removal may be performed under reduced pressure or by natural drying.

After the organic solvent is removed, a film comprising the amphiphilic block polymer A1, the hydrophobic polymer A2, the fatty acid triglyceride and the fat-soluble drug formed on the inner wall of the container. Water or an aqueous solution is added to the container to which the film is attached. The water or aqueous solution is not particularly limited, and a biochemically or pharmaceutically acceptable one may be appropriately selected by those skilled in the art. Examples thereof include distilled water for injection, normal saline, a buffer solution, and the like.

After water or an aqueous solution is added, warming treatment is performed under conditions of 20 to 90° C. and 1 to 60 minutes so that the molecular assembly is formed in the process of peeling-off of the film from the inner wall of the container. After the completion of the treatment, a dispersion liquid in which the molecular assembly (having the fat-soluble drug encapsulated therein) is dispersed in the water or aqueous solution is prepared in the container. At this time, ultrasonic treatment may be performed, if necessary.

This dispersion liquid can be directly administered to a living body. That is, the molecular assembly does not need to be stored by itself under solvent-free conditions. Therefore, the dispersion liquid is very effectively applied to, for example, a PET (Positron Emission Tomography) molecular probe using a drug having a short half-life.

When the obtained dispersion liquid is subjected to freeze-drying treatment, a method for freeze-drying treatment is not particularly limited, and any known method can be used. For example, the dispersion liquid of the molecular assembly obtained in such a manner as described above may be frozen by, for example, liquid nitrogen and sublimated under reduced pressure. In this way, a freeze-dried product of the molecular assembly is obtained. That is, the molecular assembly can be stored as a freeze-dried product. If necessary, water or an aqueous solution may be added to the freeze-dried product to obtain a dispersion liquid of the molecular assembly so that the molecular assembly can be used. The water or aqueous solution is not particularly limited, and a biochemically or pharmaceutically acceptable one may be appropriately selected by those skilled in the art. Examples thereof include distilled water for injection, normal saline, a buffer solution, and the like.

Here, before subjected to freeze-drying treatment, the dispersion liquid may contain, in addition to the molecular assembly according to the present invention formed from the amphiphilic block polymer A1, the hydrophobic polymer A2, the fatty acid triglyceride and the fat-soluble drug, the amphiphilic block polymer A1, the hydrophobic polymer A2, the fatty acid triglyceride and the fat-soluble drug remaining as they are without forming the molecular assembly. When such a dispersion liquid is subjected to freeze-drying treatment, the molecular assembly can further be formed from the amphiphilic block polymer A1, the hydrophobic polymer A2, the fatty acid triglyceride and the fat-soluble drug remaining without forming the molecular assembly according to the present invention in the process of concentration of the solvent. Accordingly, this makes it possible to efficiently prepare the molecular assembly according to the present invention.

[5-2. Injection Method]

An injection method includes the following steps of: preparing a solution, in a container (e.g., a test tube), containing the amphiphilic block polymer A1, the hydrophobic polymer A2, the fatty acid triglyceride and the fat-soluble drug in an organic solvent; dispersing the solution in water or an aqueous solution; and removing the organic solvent. In the injection method, the step of purification treatment may be appropriately performed before the step of removing the organic solvent.

Examples of the organic solvent used in the injection method include trifluoroethanol, ethanol, 2-propanol, hexafluoroisopropanol, dimethylsulfoxide, dimethylformamide, and the like.

Examples of the water or aqueous solution used include distilled water for injection, normal saline, a buffer solution, and the like.

Examples of the purification treatment performed include gel filtration chromatography, filtering, ultracentrifugation, and the like.

When the molecular assembly to be administered to a living body is obtained in such a manner as described above using an organic solvent hazardous to a living body, removal of the organic solvent needs to be strictly performed.

When the molecular assembly is prepared as an encapsulated-type vesicle, the molecular assembly may be prepared by dissolving or suspending a substance to be encapsulated in a water-based solvent such as distilled water for injection, normal saline, or a buffer solution to obtain an aqueous solution or suspension; and dispersing, into the aqueous solution or suspension, a solution obtained by dissolving the amphiphilic block polymer A1, the hydrophobic polymer A2, the fatty acid triglyceride and the fat-soluble drug in the above-mentioned organic solvent.

[6. Drug Delivery System]

Drug delivery can be conducted by administration of the molecular assembly according to the present invention to a living body.

The administration target in the drug delivery method in the present invention is not particularly limited. Particularly, the molecular assembly according to the present invention is excellent in specific accumulation in a cancer site. The molecular assembly according to the present invention accumulates in cancer tissue due to EPR (enhanced permeability and retention) effect, and therefore its accumulation does not depend on the kind of cancer. Accordingly, the administration target of the molecular assembly according to the present invention is preferably a cancer. Examples of the cancer as the administration target include a wide variety of cancers such as a liver cancer, a pancreas cancer, a lung cancer, a uterine cervical cancer, a breast cancer, and a colon cancer.

Accumulation of the molecular assembly of the present invention in a cancer site greatly relies on the design of the molecular assembly capable of achieving particle diameter control with which renal excretion and accumulation into the reticuloendothelial system such as liver are avoided, and the molecular design of the amphiphilic polymer capable of achieving particle surface control for imparting the stealth characteristics to the reticuloendothelial system.

EXAMPLES

Hereinbelow, the present invention will be described in more detail with reference to examples, but the present invention is not limited thereto.

[Amphiphilic Block Polymer A1]

The amphiphilic block polymer A1 can be synthesized with reference to a method described in WO 2009/148121 A and WO 2012/176885 A.

(PSar$_{70}$-PLLA$_{30}$)

As shown by the following chemical formula, aminated poly-L-lactic acid (a-PLLA) (average polymerization degree: 30) was first synthesized using L-lactide (compound 1) and N-carbobenzoxy-1,2-diaminoethane hydrochloride (compound 2).

[Chemical formula 3]

a-PLLA

Then, sarcosine-NCA (Sar-NCA) and aminated poly-L-lactic acid (a-PLLA) were reacted using glycolic acid, O-(benzotriazol-1-yl)-N,N,N',N'-tetramethyluronium hexafluorophosphate (HATU), and N,N-diisopropylethylamine (DIEA) to synthesize a linear amphiphilic block polymer (PSar$_{70}$-PLLA$_{30}$) comprising a hydrophilic block having 70 sarcosine units and a hydrophobic block having 30 L-lactic acid units.

[Chemical Formula 4]

a-PLLA

PSar$_{70}$-PLLA$_{30}$

[Hydrophobic Polymer A2]

The hydrophobic polymer A2 can be synthesized with reference to, for example, WO 2009/148121A ([0235] to [0243]).

(Z-PLLA30)

Poly-L-lactic acid (average polymerization degree: 30, weight average molecular weight MW=2,356) represented as Z-PLLA was synthesized using L-lactide (compound 1) and N-carbobenzoxy-1,2-diaminoethane hydrochloride (compound 2). The number of L-lactic acid units in Z-PLLA: 30.

[Chemical formula 5]

Z-PLLA

[Miriplatin]

C$_{34}$H$_{68}$N$_2$O$_4$Pt (molecular weight: 763.99)

[Chemical formula 6]

Experimental Example 1: Preparation of Miriplatin-Encapsulated Lactosome 1: with or without Addition of Middle-Chain Fatty Acid Triglyceride In a glass test tube, 100 mol % (on the basis of the molar number of $PSar_{70}$-$PLLA_{30}$) of Z-$PLLA_{30}$, 5 wt % (0.1 mg) of miriplatin (available from Sumitomo Dainippon Pharma Co., Ltd.), and 30 wt % (0.6 mg) of ODO [(caprylic acid/capric acid) triglyceride] (available from The Nisshin OilliO Group, Ltd.) were added to 2 mg of $PSar_{70}$-$PLLA_{30}$, and dissolved in about 0.5 mL of chloroform, and the solvent was distilled off under reduced pressure, to provide a film on the inner wall of the test tube. To the obtained film, 2 mL of ultrapure water was added, and subjected to a heating treatment at 85° C. for 20 minutes, to conduct particulation. The obtained liquid containing particles was subjected to a filtering treatment with a filter of 0.2 μm, to give a liquid containing miriplatin-encapsulated lactosome (sample 4).

For comparison, particulation and a filtering treatment were carried out in the same manner as the operation described above except that ODO was not added, to give a liquid containing miriplatin-encapsulated lactosome (sample 1).

For the sample 1 (without addition of ODO) and the sample 4 (with addition of 30 wt % ODO), a lactosome particle diameter and an encapsulated amount of miriplatin were determined. The result is shown in Table 1.

The particle diameter of the lactosome nanoparticles was measured by dynamic light scattering (DLS). The measurement was performed using a dynamic light scattering measuring instrument (manufactured by Malvern Instruments, Zetasizer Nano).

The encapsulated amount of miriplatin in lactosome was quantified by ICP-MS measurement of $^{195}Pt$ contained in miriplatin.

TABLE 1

|  | Particle diameter (nm) | Encapsulated Amount of Miriplatin (wt. %) |
|---|---|---|
| Sample 1 | 57.8 | 1.52 |
| Sample 4 | 82.4 | 3.71 |

As shown in Table 1, the encapsulated amount of miriplatin in lactosome of the case with addition of 30 wt % ODO (sample 4) was 3.71 wt %, and the encapsulated amount of miriplatin increased about 2.4 folds compared with the case without addition of ODO (sample 1). Also, the particle diameter increased from 57.8 nm to 82.4 nm by addition of ODO.

Experimental Example 2: Preparation of Miriplatin-Encapsulated Lactosome 2: Evaluation of Adding Amount of Middle-Chain Fatty Acid Triglyceride For evaluating the optimum adding amount of ODO to lactosome, miriplatin was encapsulated while the adding amount of ODO to the amphiphilic polymer was varied in a range of 0 to 60 wt %. (Z-$PLLA_{30}$ amount: 100 mol %, miriplatin amount: 5 wt %)

That is, particulation and a filtering treatment were carried out in the same manner as the operation described in the Example 1 except that the adding amount of ODO to $PSar_{70}$-$PLLA_{30}$ was 0 wt % (sample 1: the same as sample 1 for comparison in Experimental example 1), 5 wt % (sample 2), 15 wt % (sample 3), 30 wt % (sample 4: the same as sample 4 in Experimental example 1), 40 wt % (sample 5), 50 wt % (sample 6), or 60 wt % (sample 7), to obtain respective liquids containing miriplatin-encapsulated lactosome (samples 1 to 7).

For each of the samples 1 to 7, scattering intensity from micelle, and scattering intensity from agglomerated miriplatin were measured by a dynamic scattering method (Zetasizer Nano, available from Malvern Instruments). Then the scattering intensity ratio=(scattering intensity from micelle)/(scattering intensity from agglomerated miriplatin) was determined to give the following result.

|  | Adding amount of ODO | Scattering intensity ratio |
|---|---|---|
| Sample 1 | 0 wt % | 0.60 |
| Sample 2 | 5 wt % | 0.48 |
| Sample 3 | 15 wt % | 1.10 |
| Sample 4 | 30 wt % | 2.25 |
| Sample 5 | 40 wt % | 1.60 |
| Sample 6 | 50 wt % | 0.75 |
| Sample 7 | 60 wt % | 0.60 |

Figure 1:
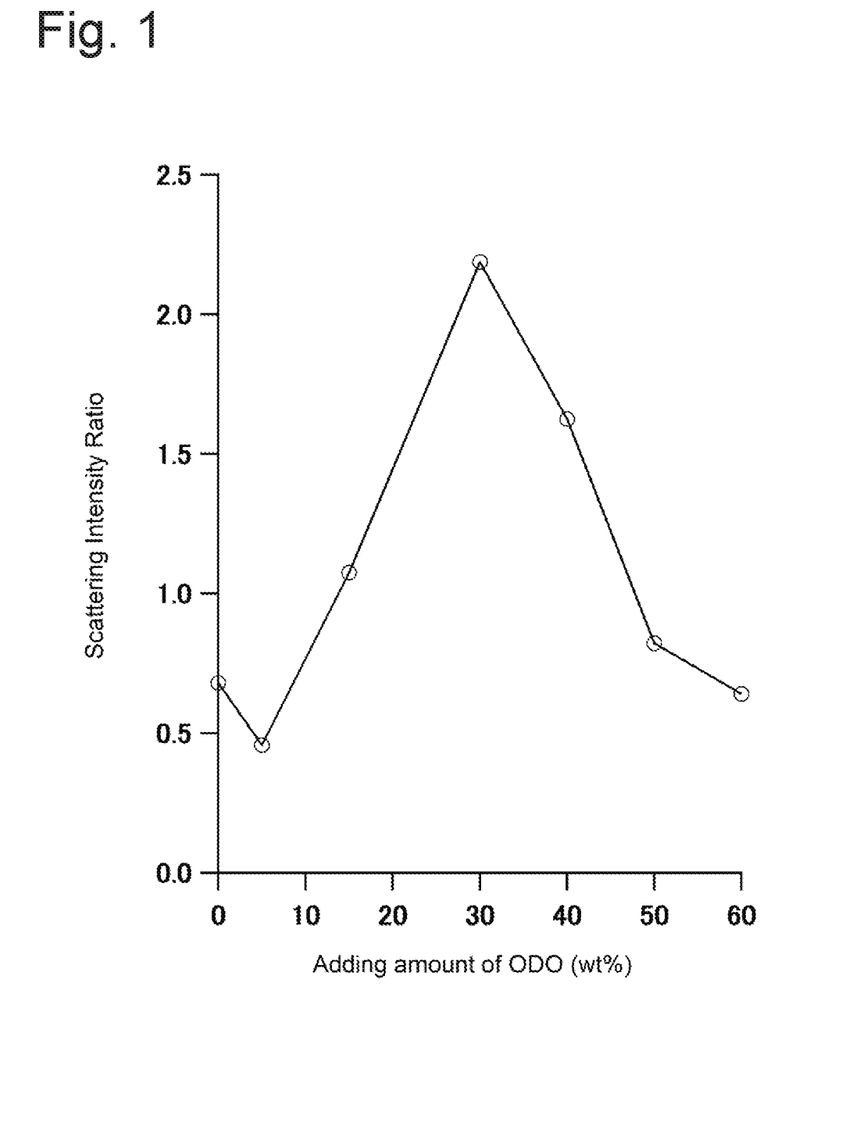
FIG. 1 is a graph showing the ratio of scattering intensity [(scattering intensity from micelle)/(scattering intensity from agglomerated miriplatin)] to adding amount of ODO in Experimental example 2.

FIG. 1 is a graph showing the scattering intensity ratio to the adding amount of ODO (wt %). These results revealed that the scattering intensity from micelle peaks at the adding amount of ODO of 30 wt %. The reason is considered as follows. When the adding amount of ODO was small, the effect of adding ODO was weak, so that miriplatin was not sufficiently encapsulated in lactosome, and the agglomerated miriplatin was generated. On the other hand, when the adding amount of ODO was large, agglomerate derived from ODO that was not encapsulated in lactosome was generated, so that miriplatin was not sufficiently encapsulated in lactosome, and the agglomerated miriplatin was generated. It is considered that the adding amount of ODO with respect to $PSar_{70}$-$PLLA_{30}$ is preferably about 15 to 45 wt %.

Experimental Example 3: Preparation of Miriplatin-Encapsulated Lactosome 3: Evaluation of Addition of Polylactic Acid In this experimental example, encapsulation tests were conducted while the mixing amount of miriplatin to the amphiphilic polymer was varied, 10 wt %, 5 wt %, or 2 wt % for the case where polylactic acid was added to the amphiphilic polymer (50 mol % or 100 mol % on the basis of the molar number of the amphiphilic polymer) and for the case where polylactic acid was not added (0 mol %). (Without addition of middle-chain fatty acid triglyceride)

In a test tube, 0 mol %, 50 mol %, or 100 mol % of Z-$PLLA_{30}$ was charged with respect to 2 mg of $PSar_{70}$-$PLLA_{30}$, and for each case, 10 wt % (0.2 mg), 5 wt % (0.1 mg), or 2 wt %(0.04 mg) of miriplatin (available from Sumitomo Dainippon Pharma Co., Ltd.) was added, and dissolved in about 0.5 mL of chloroform, and the solvent was distilled off under reduced pressure, to provide a film on the inner wall of the test tube. To the obtained film, 2 mL of ultrapure water was added and an ultrasonic treatment (28 kHz, 60° C., 10 minutes) was conducted to granulate the film. The obtained liquid containing particles was subjected to a filtering treatment with a filter of 0.2 μm.

When miriplatin was added in an amount of 10 wt %, clogging of the filter occurred for every molar amount of polylactic acid Z-$PLLA_{30}$. Therefore, the subsequent investigation was not conducted.

For the liquid containing miriplatin-encapsulated particles after the filtering treatment when miriplatin was added in an amount of 5 wt % or 2 wt %, a particle diameter was measured by the dynamic scattering method in the same manner as Experimental example 1. When the adding amount of miriplatin was 5 wt %, the tendency that the particle diameter increases from 43.2 nm, 52.3 nm, to 76.4 nm as the adding amount of polylactic acid Z-PLLA$_{30}$ increases from 0 mol %, 50 mol %, to 100 mol %. On the other hand, when the adding amount of miriplatin was 2 wt %, particle diameters of two components were observed, and particles of about 300 nm were detected.

Then, a liquid containing miriplatin-encapsulated particles after the filtering treatment when the adding amount of miriplatin was 5 wt % or 2 wt % was lyophilized. The lyophilized miriplatin-encapsulated lactosome particles were dissolved in about 0.5 mL of chloroform, and subjected to gel filtration, and an encapsulated amount of miriplatin (wt % with respect to the amphiphilic polymer) was quantified by HPLC. When the adding amount of miriplatin was 5 wt %, no miriplatin was encapsulated unless polylactic acid Z-PLLA$_{30}$ was added, and the encapsulated amount tended to increase from 1.2 wt % to 2.0 wt % as the adding amount of polylactic acid increased from 50 mol % to 100 mol %. In contrast, when the adding amount of miriplatin was 2 wt %, dependency of the encapsulated amount of miriplatin on the adding amount of polylactic acid was not observed.

These results indicate that the composition showing the highest encapsulated amount of miriplatin was the case of adding 100 mol % of polylactic acid to the amphiphilic polymer and adding 5 wt % of miriplatin, and the miriplatin was encapsulated in an amount of 2 wt % with respect to the amphiphilic polymer in the lactosome particles. In this case, the recovery of miriplatin with respect to the loading amount was 40%.

These results are shown as Entries 1 to 6 in Table 2.

Experimental Example 4: Preparation of Miriplatin-Encapsulated Lactosome 4: Investigation of Additive In this experimental example, additives for encapsulating miriplatin were investigated.

As an additive for miriplatin-encapsulated lactosome, NIKKOL IPM-100 (isopropyl myristate, available from Nikko Chemicals Co., Ltd.), NIKKOL DES-SP (diethyl sebacate, available from Nikko Chemicals Co., Ltd.), or middle-chain fatty acid triglyceride (O.D.O, available from The Nisshin OilliO Group, Ltd.) that is often used as an injection solvent was used.

In a glass test tube, 0 mol % or 100 mol % (on the basis of the molar number of PSar$_{70}$-PLLA$_{30}$) of Z-PLLA$_{30}$, 5 wt % (0.1 mg) of miriplatin (available from Sumitomo Dainippon Pharma Co., Ltd.), and NIKKOL IPM-100, NIKKOL DES-SP, or ODO as an additive in an amount of 5, 15 or 30 wt % were added to 2 mg of PSar$_{70}$-PLLA$_{30}$, and dissolved in about 0.5 mL of chloroform, and the solvent was distilled off under reduced pressure, to provide a film on the inner wall of the test tube. To the obtained film, 2 mL of ultrapure water was added and a heating treatment at 85° C. for 20 minutes was conducted to granulate the film, and thus a liquid containing particles was obtained. For the case where 100 mol % of Z-PLLA$_{30}$, and 5 wt % (0.1 mg) of miriplatin (available from Sumitomo Dainippon Pharma Co., Ltd.), and ODO as an additive in an amount of 40, 50, or 60 wt % were added, particulation was conducted in the same manner.

For each case, the transparency in the state of a film was highest when ODO+Z-PLLA$_{30}$ was added.

Each liquid containing particles was subjected to a filtering treatment with a filter of 0.2 μm. In three cases, IPM-100 5 wt % (Entry 7), DES-SP 5 wt % (Entry 8), and ODO 30 wt %+Z-PLLA$_{30}$ (Entry 9), the whole amount passed through the filter, and in other liquids containing particles, the filter was clogged. Further, the sample in which the particles are composed of the same component was only ODO 30 wt %+Z-PLLA$_{30}$ (Entry 9). In ODO 40 wt %+Z-PLLA$_{30}$ (Entry 10), the filter was clogged, and when the adding amount of ODO was further increased to 50 wt % or more, the liquid containing particles no longer passed through the filter. The particle diameter of ODO 30 wt %+Z-PLLA$_{30}$ (Entry 9) was 82.4 nm, and the particle diameter increased compared with the particle diameter of 57.8 nm in the case of not adding ODO (sample 1 in Table 1). This is assumed to be due to the amphiphilic polymer acting as an emulsifier that disperses the fine agglomerate of ODO and miriplatin.

These results of miriplatin encapsulation are shown as Entries 7 to 10 in Table 2. In every case, ultrapure water was used as the solvent in particulation.

TABLE 2

|   | Psar-PLLA (mg) | Z-PLLA (mol %) | Additive | Miriplatin (wt %) | Solvent for film formation | Particulation Method | Encapsulated Amount (wt %) | Particle Diameter (nm) |
|---|---|---|---|---|---|---|---|---|
| 1 | 2 | 0 | none | 5 | chloroform | Ultrasonic treatment | 0.0 | 43.23 |
| 2 | 2 | 50 | none | 5 | chloroform | Ultrasonic treatment | 1.2 | 52.32 |
| 3 | 2 | 100 | none | 5 | chloroform | Ultrasonic treatment | 2.0 | 76.46 |
| 4 | 2 | 0 | none | 2 | chloroform | Ultrasonic treatment | 1.6 | Two components |
| 5 | 2 | 50 | none | 2 | chloroform | Ultrasonic treatment | 1.2 | Two components |
| 6 | 2 | 100 | none | 2 | chloroform | Ultrasonic treatment | 1.6 | 125.3 |
| 7 | 2 | 0 | IPM-100 5% | 5 | chloroform | Heating treatment | — | Two components |
| 8 | 2 | 0 | DES 5% | 5 | chloroform | Heating treatment | — | Two components |
| 9 | 2 | 100 | ODO 30% | 5 | chloroform | Heating treatment | 3.71 | 82.38 |
| 10 | 2 | 100 | ODO 30% | 5 | chloroform | Heating treatment | — | 88.06 |

Experimental Example 5: Evaluation of Stability of Miriplatin-Encapsulated Lactosome Stability of encapsulation of miriplatin in lactosome was evaluated by HPLC&ICP-MS in the following manner for the samples prepared by dissolving a lyophilized product of a liquid containing miriplatin-encapsulated lactosome (prepared by adding 100 mol % of Z-PLLA$_{30}$, 5 wt % of miriplatin, and 30 wt % of ODO to PSar$_{70}$-PLLA$_{30}$) prepared in Entry 9 of Experimental example 4 in phosphate buffered saline (PBS) with or without addition of bovine serum albumin (BSA).

In 0.2 ml of a miriplatin-encapsulated lactosome solution prepared by dissolving the lyophilized product of the liquid containing miriplatin-encapsulated lactosome prepared in Entry 9 of Experimental example 4 in PBS to have a concentration of 5 mg/ml, 0.5 ml of a 10 mg/ml BSA solution and 0.3 ml of a PBS solution were added. Then, stability of encapsulation of miriplatin in lactosome at 37° C. up to 192 hours was measured by HPLC&ICP-MS.

Figure 2:
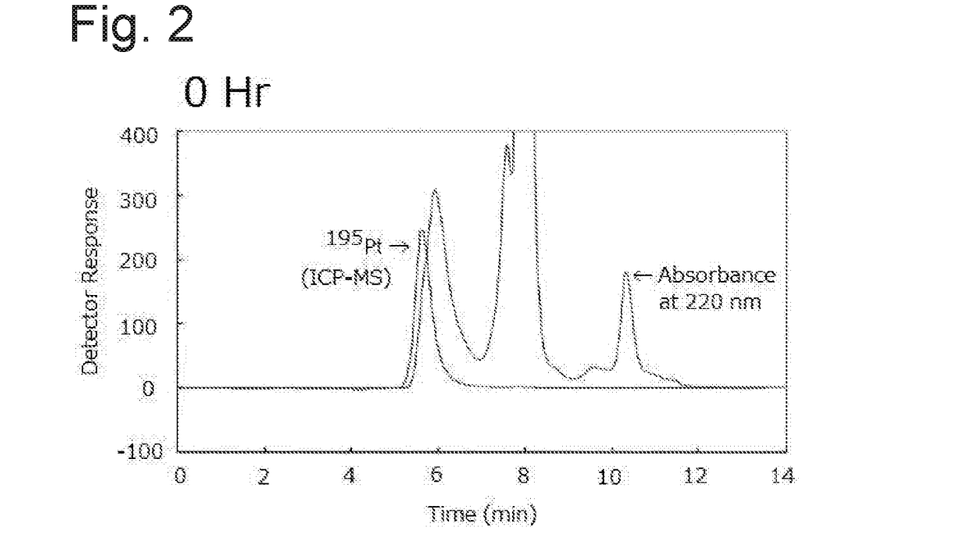
FIG. 2 is an HPLC&ICP-MS measurement chart at 0 hour. The horizontal axis indicates a retention time (min) of HPLC, the vertical axis indicates a detector response, indicating a relative intensity of $^{195}$Pt (ICP-MS) and a relative intensity of absorbance at 220 nm.
Figure 3:
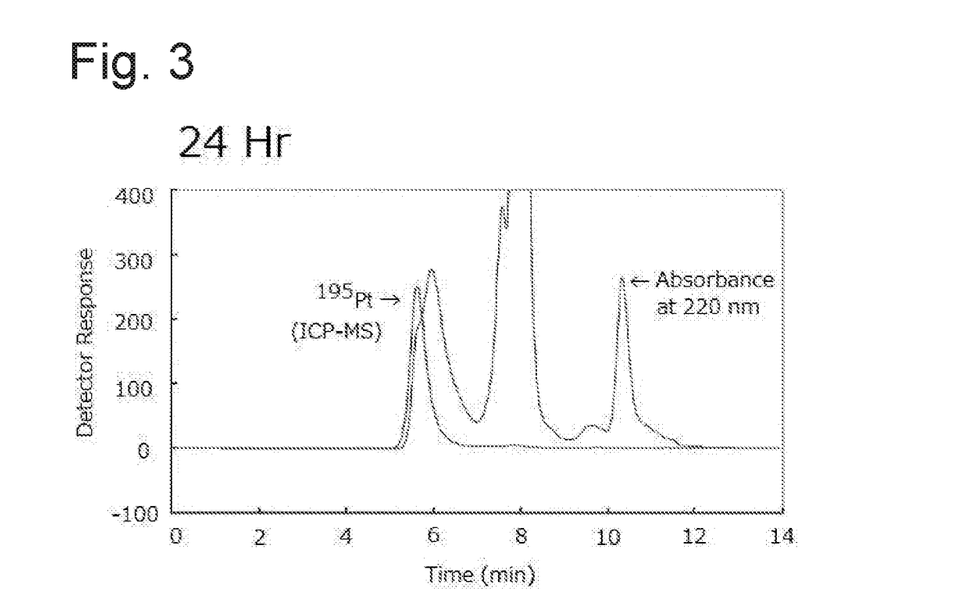
FIG. 3 is an HPLC&ICP-MS measurement chart at 24 hours.
Figure 4:
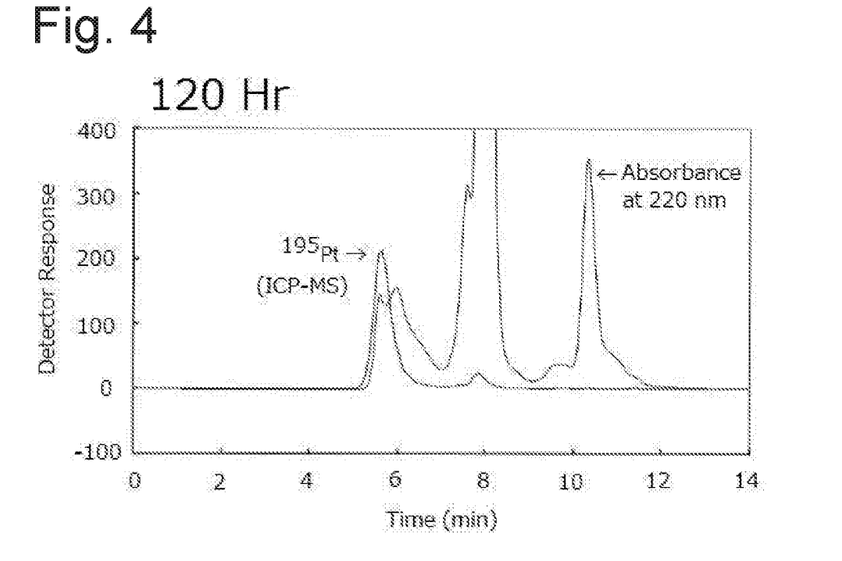
FIG. 4 is an HPLC&ICP-MS measurement chart at 120 hours.
Figure 5:
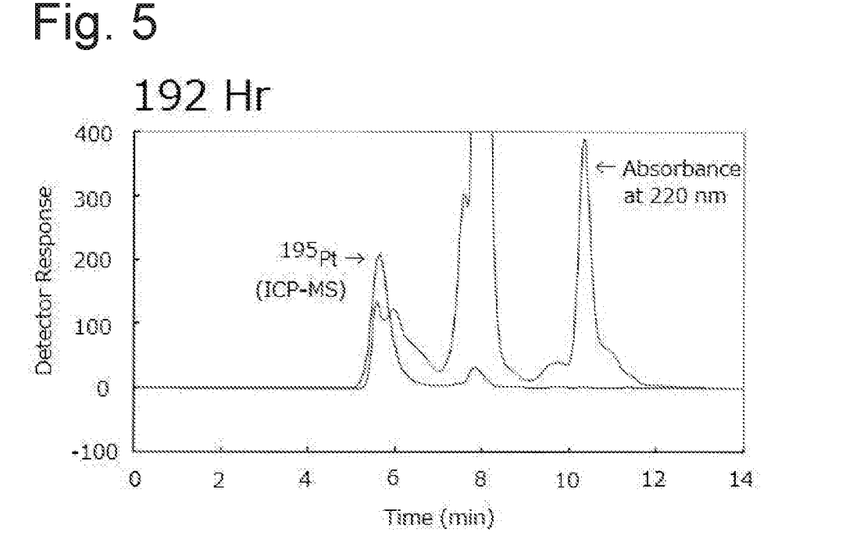
FIG. 5 is an HPLC&ICP-MS measurement chart at 192 hours.

FIGS. 2 to 5 are time-varying HPLC&ICP-MS measurement charts at 37° C. for a solution of the miriplatin-encapsulated lactosome in PBS in the presence of albumin, and FIG. 2 is an HPLC&ICP-MS measurement chart at 0 hour, FIG. 3 is an HPLC&ICP-MS measurement chart at 24 hours, FIG. 4 is an HPLC&ICP-MS measurement chart at 120 hours, and FIG. 5 is an HPLC&ICP-MS measurement chart at 192 hours. The horizontal axis indicates a retention time (min) of HPLC, the vertical axis indicates a relative intensity of $^{195}$Pt (ICP-MS) and a relative intensity of absorbance at 220 nm.

Figure 6:
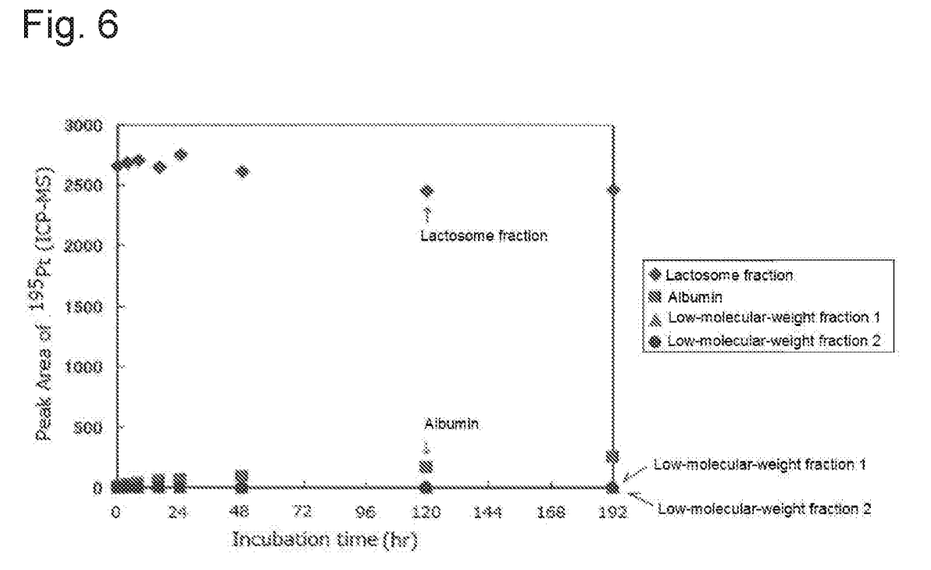
FIG. 6 is a graph showing the change in peak area of $^{195}$Pt in the time-varying ICP-MS measurement at 37° C. for a solution of miriplatin-encapsulated lactosome in PBS in the presence of albumin in Experimental example 5. The horizontal axis indicates a lapse time (hour), and the vertical axis indicates a relative peak area of $^{195}$Pt.

FIG. 6 is a graph showing the change in peak area of $^{195}$Pt in the time-varying ICP-MS measurement at 37° C. for the solution of the miriplatin-encapsulated lactosome in PBS in the presence of albumin. The horizontal axis indicates a lapse time (hour), and the vertical axis indicates a relative peak area of $^{195}$Pt.

The measurement results of HPLC and ICP-MS reveal that the miriplatin-encapsulated lactosome is a mixture of large particles and small particles, and miriplatin is retained inside the large particles. In the graph of absorbance at 220 nm, the peak at the retention time of about 5.5 minutes corresponds to the large particles, and the peak at the retention time of about 6.2 minutes corresponds to the small particles. The peak at the retention time of about 10.5 minutes or the like is a peak corresponding to a lower molecular weight fraction (low molecular weight fraction 1 and low molecular weight fraction 2 in FIG. 6) than the lactosome particles. The peak at the retention time of about 8 minutes is a peak of albumin. The absorbance peak area at 220 nm of lactosome (about 5.5 minutes, about 6.2 minutes) is kept at about 60% after 192 hours (8 days) on the basis of 0 hour, and was stable.

On the other hand, the platinum amount in the lactosome fraction remained at about 90% even after 192 hours (8 days), and the released platinum complex was detected in the albumin fraction (FIG. 6). The HPLC results in FIG. 2 to 5 showed that larger time-varying reduction was observed in the fraction having a small particle diameter than in the fraction having a large particle diameter, and the change in peak shape of lactosome was recognized. These results revealed that stability of miriplatin-encapsulated lactosome (lactosome having a large particle diameter) is higher in the presence of albumin.

Also for the case in the absence of albumin, stability of miriplatin-encapsulated lactosome was evaluated in the same manner at 37° C. up to a lapse of 192 hours. The peak area of lactosome reduced with time and only about 20% remained after 192 hours (8 days), and the low molecular weight fraction increased with time. The amount of platinum in the lactosome fraction showed more rapid reduction compared with the peak area of lactosome. Thus, in the absence of albumin, stability of the miriplatin-encapsulated lactosome was inferior to that in the presence of albumin.

The invention claimed is:

1. A molecular assembly comprising:
   an amphiphilic block polymer A1 comprising a hydrophilic block having a sarcosine unit and a hydrophobic block having a lactic acid unit;
   a hydrophobic polymer A2 having a lactic acid unit;
   a fatty acid triglyceride; and
   a fat-soluble drug,
   wherein the amphiphilic block polymer A1 is the hydrophobic polymer A2 is the fatty acid triglyceride is (caprylic acid/capric acid) triglyceride, and
the fat-soluble drug is (SP-4-2)-[(1R,2R)-cyclohexane-1,2-diamine-N,N'] bis(tetradeanoate-O) platinum],
wherein the hydrophobic polymer A2, the fatty acid triglyceride, and the fat-soluble drug exist in a hydrophobic core part of the molecular assembly composed of the amphiphilic block polymer A1, and
wherein the fatty acid triglyceride is in an amount of 15 to 45 wt % with respect to an amount of the amphiphilic block polymer A1.

2. The molecular assembly according to claim 1, wherein a molar ratio A2/A1 of the hydrophobic polymer A2 to the amphiphilic block polymer A1 is in a range of 0.1/1 to 10/1.

3. The molecular assembly according to claim 1, wherein the fat-soluble drug is contained in an amount of 1 to 50% by weight with respect to an amount of the amphiphilic block polymer A1.

4. The molecular assembly according to claim 1, which has a particle diameter of 10 to 1,000 nm.

5. The molecular assembly according to claim 1, which is obtained by a preparation method comprising the steps of:
   preparing a solution, in a container, containing the amphiphilic block polymer A1, the hydrophobic polymer A2, the fatty acid triglyceride and the fat-soluble drug in an organic solvent;
   removing the organic solvent from the solution to obtain a film comprising the amphiphilic block polymer A1, the hydrophobic polymer A2, the fatty acid triglyceride and the fat-soluble drug on an inner wall of the container; and
   adding water or an aqueous solution into the container to convert the film into a particulate molecular assembly, thereby obtaining a dispersion liquid of the molecular assembly.

* * * * *